US00PP13190P2

(12) United States Plant Patent
Utecht

(10) Patent No.: US PP13,190 P2
(45) Date of Patent: Nov. 5, 2002

(54) GERANIUM PLANT NAMED 'FISTWI'

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/991,912

(22) Filed: Nov. 26, 2001

(65) Prior Publication Data

US 2002/0083505 P1 Jun. 27, 2002

(51) Int. Cl.[7] ..... A01H 5/00

(52) U.S. Cl. ..... Plt./330

(58) Field of Search ..... Plt./330

*Primary Examiner*—Kent L. Bell
(74) *Attorney, Agent, or Firm*—Foley & Lardner

(57) ABSTRACT

A new and distinct cultivar of geranium plant named 'Fistwi', as described and illustrated, and particularly characterized by the combined features of round, semi-double, bright rose colored flowers with salmon flares, large inflorescences well above the foliage, medium green foliage with relatively strong zonation, and medium to tall plant habit.

1 Drawing Sheet

BOTANICAL CLASSIFICATION

*Pelargonium zonale.*

VARIETY DENOMINATION

'Fistwi'.

BACKGROUND OF THE INVENTION

The present invention comprises a new and distinct cultivar of geranium, botanically known as *Pelargonium zonale,* and hereinafter referred to by the cultivar name 'Fistwi'.

'Fistwi' is a product of a planned breeding program which had the objective of creating new geranium varieties with deep-salmon colored semi-double flowers in combination with medium green foliage, and medium sized to moderately tall plant habit.

'Fistwi' originated from a hybridization made by the inventor Angelika Utecht in a controlled breeding program in Galdar, Gran Canaria, Spain, in 1995. The female parent was an unpatented hybrid seedling, no. K91-1216-3, having uniform-salmon colored, single-type flowers, medium green foliage with strong zonation, and vigorous growth. The male parent of 'Fistwi' was an unpatented seedling 'I93-200-4', which was derived by self-pollinating the cultivar 'Robe', similar to the cultivar 'Sassy Dark Red' (U.S. Plant Pat. No. 8,053), which is characterized by dark-red to purple-red, semi-double flowers, medium green foliage with weak zonation, and compact plant habit. The seedling from 'Robe' was characterized by dark-pink flower color, and somewhat stronger zonation than 'Robe'.

'Fistwi' was selected as one flowering plant within the progeny of the stated cross by Angelika Utecht in 1996, in a controlled environment in Galdar, Gran Canaria, Spain.

The first act of asexual reproduction of 'Fistwi' was accomplished when vegetative cuttings were taken from the initial selection in the fall of 1996, in a controlled environment in Galdar, Gran Canaria, Spain, by, or under the supervision of, Angelika Utecht.

Horticultural examination of plants grown from cuttings of the plant initiated in May 1998 in Hillscheid, Federal Republic of Germany, and continuing thereafter, has demonstrated that the combination of characteristics as herein disclosed for 'Fistwi' are firmly fixed and are retained through successive generations of asexual reproduction. The new cultivar reproduces true to type.

'Fistwi' has not been observed under all possible environmental conditions. The phenotype may vary significantly with variations in environment such as temperature, light intensity and day length. The following observations, measurements, and comparisons describe plants grown in Hillscheid, Germany, and in Langley, British Columbia, Canada, under greenhouse conditions which approximate those generally used in commercial practice.

BRIEF DESCRIPTION OF THE INVENTION

The following traits have been repeatedly observed and are determined to be basic characteristics of 'Fistwi' in combination distinguish this geranium as a new and distinct cultivar:

1. Rose red colored, round, cup-shaped flowers;
2. Large inflorescence and long peduncles;
3. Medium green foliage with relatively strong zonation;
4. Moderately vigorous growth, and medium to tall plant habit; and
5. Medium, mid season spring flowering response.

Of the many commercial cultivars known to the present inventor, the most similar in comparison to 'Fistwi' is the patented cultivar 'Fispur' (U.S. Plant Pat. No. 10,350). In comparison to 'Fispur', 'Fistwi' has a lighter rose red flower color, RHS 52 A, in comparison to color value between 52 A and 57 A for 'Fispur'. Additionally, 'Fistwi' has distinct orange flares at the bases of upper petals, which lack with 'Fispur'. Furthermore, 'Fistwi' has larger leaves with somewhat stronger zonation.

BRIEF DESCRIPTION OF THE DRAWING

The accompanying photographic drawing shows typical flower and foliage characteristics of 'Fistwi' with colors being as true as possible with an illustration of this type. The drawing shows a flowering pot plant in a 14 cm container.

DETAILED BOTANICAL DESCRIPTION

In the following description color references are made to The Royal Horticultural Society Colour Chart (R.H.S.). The color values were determined indoors from plants developed in a greenhouse in May 2001, in Hillscheid, Germany. The measurements were taken in Langley, British Columbia, Canada, in early July, 2001, 18 weeks after planting of rooted cuttings. The plants were growing in 8 inch containers and had not been pinched.

Inflorescence:
- *Type*.—Umbel.
- *Shape*.—Semi-spherical.
- *Average diameter*.—132 mm.
- *Average depth*.—58 mm.
- *Peduncle length*.—190 mm.
- *Peduncle color*.—Green, RHS 144 A, no anthocyanin.
- *Pedicel length*.—33.5 mm.
- *Pedicel color*.—Green, RHS 144 A to RHS 144 B.
- *Number of flowers per umbel*.—About 30.

Corolla:
- *Average diameter*.—48.0 mm.
- *Form*.—Semi-double.
- *Shape*.—Round, flat.
- *Number of petals*.—8.6.
- *Number of petaloids*.—0–1, narrow, upper surface is RHS 52 A with RHS 155 D base, lower surface is RHS 55A with RHS 155 D base.
- *Shape of petals*.—Obovate, base attenuate, upper end is truncate or rounded, margin is entire or very weakly serrulated at the apex.
- *Size of petals*.—Upper petals length 24–25 mm, width 20–23 mm lower petals length 23–24 mm, width 23 mm.
- *Color* (*general tonality from a distance of three meters*).—Rose red with a trace of salmon at the bases of the upper petals.
- *Color of upper petals*.—Main part RHS 52 A.
- *Markings of upper petals*.—Salmon-orange base, RHS 44 C.
- *Color of lower petals*.—Between RHS 52 A and RHS 57 C.
- *Markings of lower petals*.—None.
- *Color of lower surface of petals*.—Upper petals mainly RHS 50 A, lower petals RHS 55 A.
- *Color of sepals*.—Outer surface light green, RHS 144 B, inner surface light green, RHS 144 B.
- *Number of sepals*.—5.
- *Shape of sepals*.—Linear to lanceolate, acute tip, truncate base, surface with very short pubescence, margin entire.
- *Size of sepals*.—10–12 mm long, 4 mm wide for the largest upper sepal, 2–3 mm in width for the other sepals.

Bud: (just before petals unfold):
- *Shape*.—Elliptical.
- *Color* (*sepals*).—Green, RHS 144 B.
- *Color* (*petals*).—Marbled, pink RHS 54 A, and almost white, RHS 49 D.
- *Length*.—19 mm.
- *Width*.—12 mm.

Reproductive organs:
- *Androecium*.—5–7 fertile anthers, filaments white, RHS 155 A, moderate pollen, orange, RHS 30 A.
- *Gynoecium*.—One pistil, style and stigma red, RHS 46 B, 5 to 6 lobed stigma.
- *Fertility/seed set*.—In late summer and fall a few seeds are developed. Fruit: Oblong, about 6 mm in diameter, with rostrum (beak), total length about 40 mm. Seed: Oblong, 4–5 mm long, brown RHS 177 B.

Spring flowering response period: In Hillscheid, Germany, in 2000 plants had on average 1.2 flowers opened 8 weeks after planting of rooted cuttings.

Outdoor flower production: Continuously flowering, and relatively rich flowing, the flower count in 2000 in Hillscheid, Germany, indicated about 2.9 inflorescences per plant in mid May.

Durability: Good stability of flower color, good rain resistance.

Lastingness of the individual flower: About 8–9 days at 18° C., about 18–20 days for the umbel.

Pest/disease resistance/susceptibility: No observations made to date.

Fragrance: None.

PLANT

Foliage:
- *Shape*.—Kidney-shaped, with open, cordate base, and weak lobes.
- *Margin*.—Bicrenated, somewhat wavy.
- *Texture*.—Upper surface smooth, velvety.
- *Size of leaf*.—101 mm wide, 57.5 mm long.
- *Color of upper surface*.—Medium green, approximately RHS 137 B to RHS 137 C.
- *Color of zonation*.—Brown, about RHS 166 A.
- *Color of lower surface*.—RHS 137 D.
- *Petioles*.—50–60 mm long, 3 mm in diameter, light green in color, approximately RHS 144 A to RHS 144 B.

General appearance and form:
- *Stem color*.—Green, RHS 144 B to RHS 144 C.
- *Internode length*.—15–25 mm.
- *Branching pattern*.—Average 6.6 branches.
- *Size of plants*.—Height 30.2 cm, measured from the top of the soil (base of the main stem) to the surface of the foliage canopy, without inflorescences; width 44.2 cm.

I claim:

1. A new and distinct cultivar of geranium plant named 'Fistwi', as described and illustrated herein.

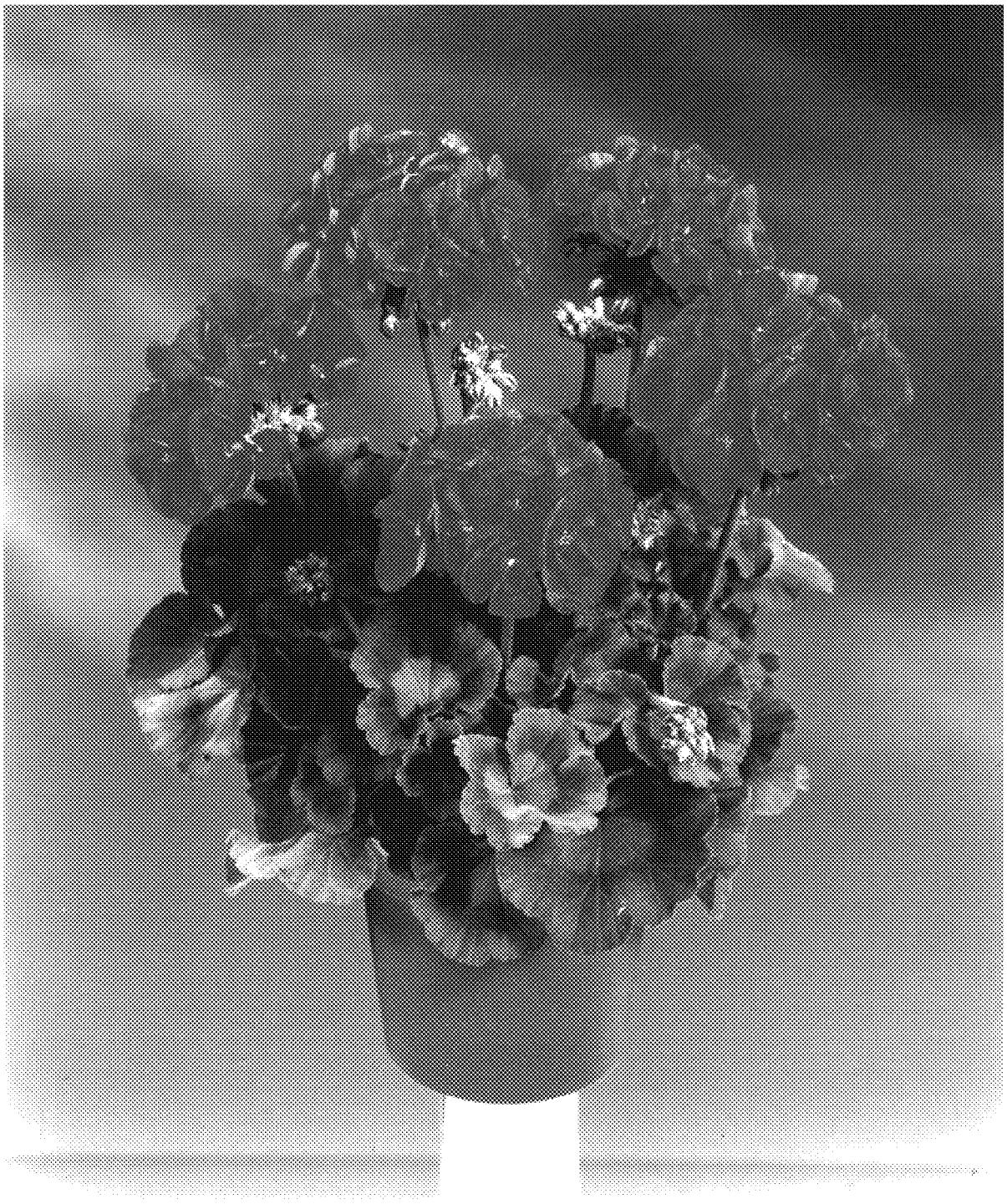

* * * * *